US00PP33236P2

(12) United States Plant Patent
von Tubeuf

(10) Patent No.: US PP33,236 P2
(45) Date of Patent: Jul. 6, 2021

(54) POINSETTIA PLANT NAMED 'NPCW19287'

(50) Latin Name: *Euphorbia pulcherrima*
Varietal Denomination: NPCW19287

(71) Applicant: Klemm+Sohn GmbH & Co. KG, Stuttgart (DE)

(72) Inventor: Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/873,270

(22) Filed: Mar. 10, 2020

(51) Int. Cl.
*A01H 5/02* (2018.01)
*A01H 6/38* (2018.01)

(52) U.S. Cl.
USPC ..... Plt./303
CPC ..... *A01H 6/385* (2018.05); *A01H 6/38* (2018.05)

(58) Field of Classification Search
USPC ..... Plt./303, 306
CPC ..... A01H 5/02
See application file for complete search history.

(56) References Cited

PUBLICATIONS https://www.beautifulflowerpictures.com/blog/poinsettias-2015-part-2/; Nov. 30, 2015; 5 pages.*
https://www.ballseed.com/PlantInfo/?phid=050006473004415; Jul. 31, 2020; 1 page.*
Canul-Ku, Jamie et al.; Effect of irradiation on wild poinsettia (*Euphorbia pulcherrima* Willd. ex Klotzsch) in Moreios; Rev. Mex. Cienc. Agric [online]; vol. 3, n.8, Abstract; 2012; 1 page.*
Eun Kyung Lee et al.; Rooting, growth, and color mutation of poinsettia affected by gamma radiation; Journal of Radiation Industry; vol. 4(3), Abstract; 2010; 1 page.*

* cited by examiner

*Primary Examiner* — Kent L Bell
(74) *Attorney, Agent, or Firm* — Weatherly IP Solutions, LLC; Barbara Campbell

(57) ABSTRACT

A new poinsettia plant particularly distinguished by having reddish-pink bracts and a triangular plant form and upright habit, is disclosed.

1 Drawing Sheet

Genus and species: *Euphorbia pulcherrima.*
Variety denomination: 'NPCW19287'.

BACKGROUND OF THE NEW PLANT

The present invention comprises a new and distinct variety of poinsettia, botanically known as *Euphorbia pulcherrima* and hereinafter referred to by the variety name 'NPCW19287'. 'NPCW19287' was derived from a population of irradiated plants, using Gamma-Rays 20 Gy, of the variety 'NPCW14233' (U.S. Plant Pat. No. 27,228) in November 2014.

In February 2015, 'NPCW19287' was first asexually propagated by vegetative apical cuttings in Stuttgart, Germany. 'NPCW19287' was found to reproduce true to type in successive generations of asexual propagation via vegetative apical cuttings in Stuttgart, Germany.

SUMMARY

The following are the most outstanding and distinguishing characteristics of this new variety when grown under normal horticultural practices in Stuttgart, Germany.

1. Reddish-pink bracts; and
2. A plant having a triangular plant form and upright habit.

DESCRIPTION OF THE PHOTOGRAPH

This new poinsettia plant is illustrated by the accompanying photograph which shows an overall view of the whole plant. The photograph is of a plant approximately 12-weeks-old grown indoors in Stuttgart, Germany in December 2016. The colors shown are as true as can be reasonably obtained by conventional photographic procedures.

DESCRIPTION OF THE NEW VARIETY

The following detailed descriptions set forth the distinctive characteristics of 'NPCW19287'. The data which define these characteristics were collected from asexual reproductions carried out in Stuttgart, Germany. Data was collected on plants that were 19-weeks from potting in a glass greenhouse under normal horticultural practices in Stuttgart, Germany. Color references are to The R.H.S. Colour Chart of The Royal Horticultural Society of London (R.H.S.), 5$^{th}$ edition (2007) unless where otherwise stated.

Classification:
*Family.*—Euphorbiaceae.
*Species.*—*Euphorbia pulcherrima.*
*Common name.*—Poinsettia.
*Variety.*—'NPCW19287'.

Parentage: 'NPCW14233' (U.S. Plant Pat. No. 27,228).

Plant:
*Form.*—Triangular.
*Growth habit.*—Upright.
*Height.*—25 cm to 28 cm.
*Width.*—23 cm to 28 cm.
*Average number of inflorescences per plant.*—6.
*Keeping quality.*—Good.
*Time to produce a cutting.*—4 weeks.

*Flowering response time*.—Approximately 57 days.
*Propagation type*.—Apical cuttings.
*Rooting habit and root color*.—Freely branching and white.
*Resistance and susceptibility to disease and pests*.—Not observed.

Lateral branches:
*Color*.—RHS 143C.
*Length*.—23 cm to 25 cm.
*Internode length*.—1.0 cm to 2.5 cm.
*Diameter*.—0.5 cm to 0.8 cm.
*Branching habit*.—Freely branching.
*Number of lateral branches per plant*.—6 to 7.
*Texture*.—Smooth.
*Strength*.—Sturdy.

Leaves:
*Quantity*.—5 to 7 per lateral branch.
*Arrangement*.—Alternate.
*Number of lobes on the leaf blade*.—0 to 2.
*Lobation depth*.—Shallow.
*Depth of the deepest sinus of the leaf blade*.—1 cm.
*Shape*.—Ovate.
*Apex*.—Acute.
*Base*.—Obtuse.
*Margin*.—Serrate.
*Length*.—6 cm to 11 cm.
*Width*.—3 cm to 7 cm.
*Texture* (*both upper and lower surfaces*).—Smooth.
*Vein color*.—Upper surface: Transparent. Lower surface: RHS 139D.
*Variegation*.—Absent.
*Venation pattern*.—Reticulate.
*Color*.—Mature foliage: Upper surface: RHS 139A. Lower surface: RHS N138B. Immature foliage: Upper surface: RHS 141A. Lower surface: RHS 139B.
*Leaf petiole*.—Length: 3 cm to 5 cm. Diameter: 0.2 cm to 0.3 cm. Color: Upper (part) surface: RHS 139D and dense spots and stripes (reddish) RHS 181A. Lower (part) surface: RHS 139D and only shallow spots and stripes RHS 181A. Texture: Smooth. Strength: Sturdy.

Inflorescence:
*Type and habit*.—Cluster of cyathia.
*Quantity per lateral branch*.—1.
*Position relative to foliar plane*.—Same height.
*Lastingness of inflorescence on the plant*.—3 to 4 weeks.
*Natural flowering season*.—End of November.
*Diameter*.—20 cm to 23 cm.
*Height*.—2 cm to 3 cm.
*Fragrance*.—Absent.

Bracts:
*Number of bracts per inflorescence*.—10 to 11.
*Color*.—Upper surface: RHS 5D background with RHS 46B spots. Lower surface: RHS 5D background with RHS 47B spots.
*Shape*.—Ovate.
*Apex*.—Acute.
*Base*.—Obtuse.
*Margin*.—Mostly entire.
*Size*.—Length: 5 cm to 10 cm. Width: 3 cm to 8 cm.
*Texture* (*both upper and lower surfaces*).—Smooth.
*Folding along the main vein*.—Absent.
*Twisting*.—Absent.
*Rugosity between the veins*.—Absent.
*Vein color*.—Upper surface: RHS 144B. Lower surface: RHS 144D.
*Bract petiole*.—Length: 1.5 cm to 3.0 cm. Diameter: 0.15 cm. Color: RHS 140B.

Cyme:
*Diameter*.—1.0 cm to 1.5 cm.
*Cyathia number*.—4 to 6 per inflorescence.
*Deformation of glands of the cyathium*.—Absent.
*Timing of opening of cyathia*.—End of November. First pollen appears in parallel to opening of the nectar cups; stigmas appear 2 weeks later.
*Cyathium*.—Shape: Ovate. Texture (inner and outer surfaces): Smooth. Diameter: 0.2 cm to 0.4 cm. Length: 0.3 cm to 0.6 cm. Color: RHS 142B.
*Peduncle*.—Color: RHS 142C. Length: 0.2 cm. Diameter: 0.2 cm to 0.3 cm. Texture: Smooth. Strength: Medium.
*Nectar cups*.—Number: 1 per cyathium. Diameter: 0.1 cm. Length: 0.3 cm to 0.4 cm. Color: RHS 1C. Shape: Lip-shaped. Texture (for each of the inner and outer surfaces): Smooth.

Reproductive organs:
*Stamen quantity*.—5 to 10 per cyathium.
*Stamen shape*.—Ovate.
*Filament length*.—0.25 cm.
*Filament color*.—RHS 47C.
*Pollen quantity*.—Sparse.
*Pollen color*.—RHS 11B.
*Gynoecium*.—Present. Pistil quantity per cyathium: 1. Stigma form: Divided in 2 parts. Seed and fruit: Not observed to date.

COMPARISON WITH PARENTAL LINE AND COMMERCIAL VARIETY

When 'NPCW19287' is compared to its parental line, the following differences are noted in Table 1.

TABLE 1

| Characteristic | 'NPCW19287' | 'NPCW14233' |
|---|---|---|
| Leaf length | 6.0 cm to 11.0 cm | 8.0 cm to 13.0 cm |
| Leaf width | 3.0 cm to 7.0 cm | 5.0 cm to 8.0 cm |

When 'NPCW19287' is compared with the commercial variety 'Monet Early' (patent status unknown), 'NPCW19287' flowers one week later than 'Monet Early' and has a smaller bract size than 'Monet Early'.

I claim:

1. A new and distinct variety of poinsettia plant designated 'NPCW19287' as illustrated and described herein.

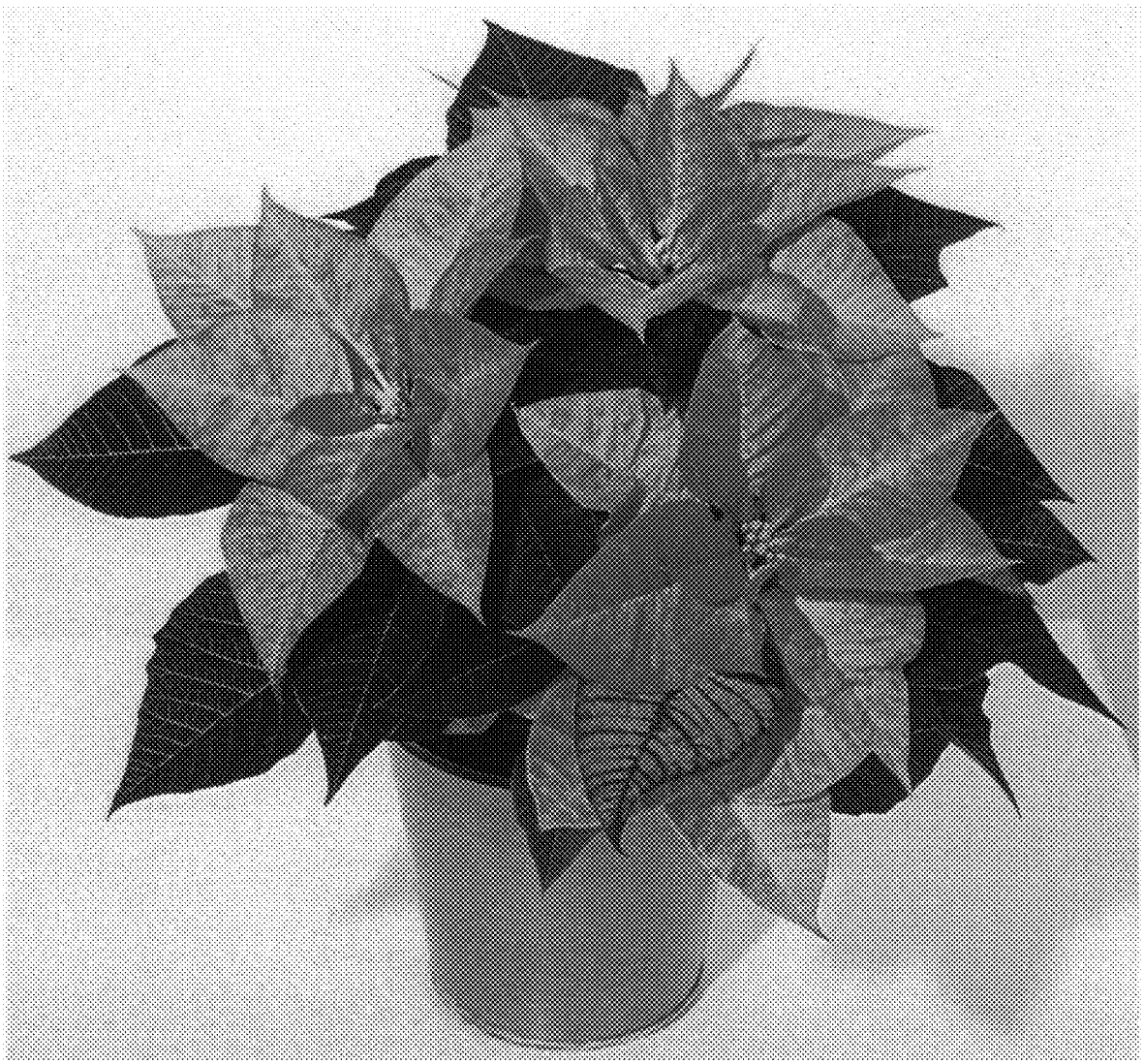

* * * * *